(12) United States Patent
Kamath et al.

(10) Patent No.: US 7,736,629 B2
(45) Date of Patent: Jun. 15, 2010

(54) RED HERBAL DENTIFRICE

(75) Inventors: Shridhara Kamath, Mumbai (IN); Ramesh Nair, Pune (IN)

(73) Assignee: Colgate-Palmolive Company, New York, NY (US)

( * ) Notice: Subject to any disclaimer, the term of this patent is extended or adjusted under 35 U.S.C. 154(b) by 1123 days.

(21) Appl. No.: 11/330,786

(22) Filed: Jan. 12, 2006

(65) Prior Publication Data

US 2007/0116652 A1    May 24, 2007

(30) Foreign Application Priority Data

Nov. 18, 2005  (IN) .................... 3081/DEL/2005

(51) Int. Cl.
*A61K 7/16* (2006.01)
(52) U.S. Cl. .......................... 424/58; 424/49
(58) Field of Classification Search ........................ None
See application file for complete search history.

(56) References Cited

U.S. PATENT DOCUMENTS

| | | | |
|---|---|---|---|
| 5,043,153 A | 8/1991 | Videki et al. | |
| 6,264,926 B1 | 7/2001 | Farooqi et al. | |
| 6,685,921 B2 * | 2/2004 | Lawlor | 424/49 |
| 2002/0031481 A1 | 3/2002 | Xu et al. | |
| 2004/0161388 A1 * | 8/2004 | Liu et al. | 424/49 |
| 2004/0247533 A1 | 12/2004 | Hosoya et al. | |
| 2005/0084551 A1 | 4/2005 | Jensen et al. | |

FOREIGN PATENT DOCUMENTS

| | | |
|---|---|---|
| JP | 2004123630 | 4/2004 |
| WO | WO 99/03445 | 1/1999 |

* cited by examiner

*Primary Examiner*—Shanon A Foley
(74) *Attorney, Agent, or Firm*—Donald L. Traut

(57) ABSTRACT

A dentifrice composition of the invention can be applied to teeth and/or gums by any conventional A dentifrice composition comprises (a) calcium carbonate having properties of particle size and angularity effective to provide mild abrasivity to dental enamel; (b) red iron oxide of low abrasivity in an effective amount on which to impart red color to the composition; and (c) a herbal component comprising at least one botanical or extract thereof, in a total herbal component amount effective to promote oral health.

14 Claims, No Drawings

RED HERBAL DENTIFRICE

BACKGROUND OF THE INVENTION

Dentifrices such as tooth powders and toothpastes containing herbal ingredients are known. An example of such a dentifrice is Red Tooth Powder, manufactured by Dabur India Ltd, and is reported to contain, inter alia, clove oil, black pepper, blend of mint oils, long pepper, ginger, camphor, tomar seed and *terminalia chebula*.

Other oral care compositions that contain antibacterial seed or pulp extract from the citrus or grape families are known. These compositions may contain additional components such as red iron oxide as a tooth cleaning cum color modifying substances, and calcium carbonate as an abrasive polishing agents.

Red color can be imparted to dentifrices by red ocher, a mineral rich in red iron oxide (anhydrous iron (III) oxide or hematite). However, red ocher is harshly abrasive to tooth enamel.

There remains a need for herbal dentifrice compositions having a pronounced red color, which can be associated in the minds of consumers with certain oral health benefits, but which exhibits a mild abrasivity to teeth and gums.

BRIEF SUMMARY OF THE INVENTION

There is now provided a dentifrice composition comprising (a) calcium carbonate having properties of particle size and angularity effective to provide mild abrasivity to dental enamel; (b) red iron oxide of low abrasivity. The red iron oxide is present in an amount sufficient to clean and/or polish the teeth and also imparts a red color to the composition. A herbal component comprising at least one botanical agent or extract thereof, is also included.

DETAILED DESCRIPTION OF THE INVENTION

The invention provides a red-colored tooth powder having an aesthetic appeal to customers but which does not exhibit the harsh abrasivity found in many conventional red colored toothpowders. Calcium carbonate is present in the composition as an abrasive to provide good dental cleaning performance. Unexpectedly, however, the calcium carbonate has also been found to result in good flavor delivery.

The calcium carbonate should be of a source and grade that imparts mild abrasivity to dental enamel. Abrasivity should be sufficient to remove surface deposits including dental plaque, but not to damage dental enamel. Typically, this requires that particle size of the calcium carbonate be in a desired range, for example having a median particle size of about 0.1 to about 30 μm, illustratively about 1 to about 20 μm or about 5 to about 15 μm. In various embodiments, particle size distribution is such that at least 99% of calcium carbonate particles have a size of about 1 to about 150 μm, about 6 to about 35 μm, or about 6 to about 13 μm. The calcium carbonate particles should typically not be highly angular, i.e., should not present many sharp edges.

Precipitated calcium carbonate, for example as described in U.S. Patent Application Publication No. 2004/0161388 (the contents of which are incorporated herein by reference) may be suitable. However, in some embodiments it is desirable to use natural calcium carbonate, derived by mechanical grinding, for example chalk, as opposed to chemical precipitation. Potential advantages of natural over precipitated calcium carbonate for use in the present composition include improved flavor release during brushing, greater cost-effectiveness in providing the desired abrasivity, and consumer preference for natural ingredients The red color of the dentifrice is provided by red iron oxide, although additional colorants may be used, if desired. The selected red iron oxide should be of low abrasivity. Crude red ocher, which typically contains clay minerals and/or other impurities in addition to the red iron oxide that gives it its color, may not be suitable for this purpose. Synthetic red iron oxide, being relatively pure and of very fine particle size, is often a suitable option. However, as in the case of calcium carbonate, it is often desired to use natural red iron oxide, derived from a mineral deposit such as red ocher. In this case, the natural red iron oxide should be of a purified grade.

The amount of red iron oxide should be effective to impart a red color to the dentifrice. The amount used in any particular case will depend on the intensity and depth of color desired. In general, a weight ratio of red iron oxide to calcium carbonate of about 1:5 to about 1:100, for example about 1:10 to about 1:50, will be found sufficient.

The blend of calcium carbonate and red iron oxide used herein enables production of a dentifrice composition having abrasivity, as determined by REA value, not greater than about 4×. In some circumstances, it may be desirable that the abrasivity is about 3.5×, about 3×, or about 2.5×, as determined by REA value. Red iron oxide as specified herein generally does not lead to staining of teeth as can occur with alternative colorants.

The herbal component of the present composition may be present in a total herbal component amount effective to promote oral health. Small quantities of flavoring oils or extracts such as oils of peppermint, cinnamon, wintergreen, etc. are widely used in dentifrices, but the total amount of such oils has generally been below an oral health promoting threshold. Promotion of oral health herein includes prevention or treatment of any one or more oral (including dental, periodontal or gingival) conditions or disorders. Such conditions or disorders illustratively and without limitation include abscess, bleeding gums, canker, caries, dental plaque, dry mouth, gingivitis, halitosis, irritation and inflammation of oral tissues (due, for example, to ill-fitting dentures), oral and dental pain (including toothache), periodontitis and pulpitis.

The herbal component comprises one or more botanicals agents or extracts thereof. A "botanical agent" as used herein is a plant or one or more parts thereof, typically in comminuted form suitable for inclusion in a composition of the invention. Botanical agents include herbs, spices and plant materials not commonly assigned to either of these categories. An "extract" as used herein is a preparation made from a botanical, the preparation comprising, generally in concentrated form, compounds that contribute to the flavor, aroma and/or biological effect (in the present context an oral health promoting effect) of the botanical agent. Extracts include without limitation essential oils, oleoresins, infusions, tinctures and natural extractives, including distillates.

The term "herbal component" herein is used for convenience to refer collectively to all ingredients of the composition that are botanicals or extracts thereof, and carries no inference that such ingredients are necessarily commingled in the composition, or that during preparation of the composition these ingredients are necessarily added together in a single premix. The term "herbal" should not be interpreted as limited to herbs (as opposed to spices or other categories of botanical agents) or extracts thereof.

While compositions of the invention can be effective in promoting at least one aspect of oral health with only a single botanical agent or extract thereof, it is generally preferred to include in the herbal component a plurality of botanical agents and/or extracts thereof. In such a case the botanical agent and/or extracts thereof can address one aspect, or more than one aspect, of oral health.

Such a plurality of botanical agents and/or extracts thereof can operate independently in promoting oral health. In a particular embodiment, however, the herbal component comprises a complex of botanicals and/or extracts thereof that cooperate in promoting oral health, for example by addressing an underlying cause of a condition, e.g., bacterial infection, and at the same time relieving symptoms of the condition, e.g., toothache or halitosis.

The total amount of the herbal component, i.e., the amount of all botanical agents and extracts thereof in the composition, can vary over a broad range, depending on the potency of individual botanicals or extracts thereof selected, on the oral health benefit targeted, and on other factors. In most cases, for each 100 parts by weight in total of calcium carbonate and red iron oxide, an amount of about 0.5 to about 20 parts by weight of the herbal component will be found effective, but greater or lesser amounts can be useful in specific situations.

Botanical agents and extracts thereof useful herein illustratively include the following:

achyranthes, *Achyranthes aspera*
aloe, *Aloe* spp., including *A. barbadensis, A. ferox* and *A. vera*
anise, *Pimpinella anisum*
aristolochia, *Aristolochia bracteolata*
arnica, *Arnica* spp., including *A. fulgens*
banyan, *Ficus bengalensis*
bakula, *Mimusops elengi*
basil, *Ocimum basilicum* and *O. minimum*
betel, *Piper betle*
black pepper, *Piper nigrum*
camphor, *Cinnamomum camphora*
catechu, *Acacia catechu*
celandine, *Chelidonium* spp.
chamomile, *Matricaria chamomilla*
chebula, *Terminalia chebula*
Chinese skullcap, *Scutellaria baicalensis*
cinnamon, *Cinnamomum lourerii* and *C. zeylandicum*
citrus, *Citrus* spp., including *C. aurantifolia, C. aurantium, C. limonum* and *C. sinensis*
clove, *Syzygium aromaticum*
dill, *Anethum* spp., including *A. graveolens* and *A. sowa*
echinacea (coneflower), *Echinacea pallida*
eucalyptus, *Eucalyptus globulus*
fennel, *Foeniculum vulgare*
gardenia, *Gardenia jasminoides*
ginger, *Zingiber officinale*
grape, *Vitis vinifera*
hop, *Humulus lupulus*
houttuynia, *Houttuynia cordata*
Indian mulberry, *Morinda citrifolia*
juniper, *Juniperus communis*
lemongrass, *Cymbopogon* spp., including *C. citratus* and *C. flexuosus*
licorice, *Glycyrrhiza* spp., including *G. glabra* and *G. uralensis*
long pepper (pipli), *Piper longum*
madhuca, *Madhuca longifolia*
magnolia, *Magnolia officinalis*
marigold, *Calendula officinalis*
mastic, *Pistacia lentiscus*
melilot, *Melilotus officinalis*
milfoil, *Achillea millefolium*
myrrh, *Commiphora* spp., including *C. abyssinica* and *C. molmol*
neem (margosa), *Azadirachta indica*
neroli (bitter orange blossom), *Citrus aurantium*
nutmeg (mace), *Myristicafragrans*
oak gall, *Quercus infectoria*
parsley, *Petroselinum sativum*
peelu, *Salvadora persica*
peppermint, *Mentha piperita*
pine, *Pinus* spp., including *P. palustris* and *P. sylvestris*
pomegranate, *Punica granatum*
prickly acacia (babul), *Acacia nilotica*
rhatany, *Krameria* spp., including *K. argentea* and *K. triandra*
rosemary, *Rosmarinus officinalis*
saffron, *Crocus sativus*
sage, *Salvia* spp., including *S. lavendulaefolia, S. officinalis* and *S. triloba*
sandalwood, *Santalum* spp., including *S. album* and *S. spicatum*
spearmint, *Mentha spicata*
spilanthes (akarkara), *Spilanthes calvi*
star anise, *Illicium verum*
tea (including green tea and oolong tea), *Camellia sinensis*
thyme, *Thymus* spp., including *T. serpyllum* and *T. vulgaris*
tomar (prickly ash), *Zanthoxylum armatum*
tulsi (holy basil), *Ocimum sanctum*
turmeric, *Curcuma longa*
usnea, *Usnea barbata*
vajradanti, *Potentilla fulgens*
walnut, *Juglans regia*
wintergreen, *Gaultheria procumbens*

Oral health promoting benefits for these and other botanicals are reported in publications cited herein and in various herbal references available in print form or on websites accessible via the internet.

In one embodiment, the composition comprises a plurality of botanicals and/or extracts thereof, wherein at least one of such botanicals is selected from basil, black pepper, camphor, chebula, clove, ginger and neem. Examples of useful extracts according to this embodiment include without limitation basil oil, black pepper oleoresin ("oleoresin piperine"), clove oil, ginger oleoresin and neem oil.

In another embodiment, the composition comprises each of basil, black pepper, camphor, chebula, clove, ginger and neem, independently in the form of crude botanical or an extract such as an oil or oleoresin. Optionally, such a composition further comprises one or both of peppermint and eucalyptus, for example as peppermint and eucalyptus oils.

A tooth powder can be prepared comprising calcium carbonate, red iron oxide and a herbal component as described above. No other ingredients are necessary but can be added if desired. Such a tooth powder typically comprises:

calcium carbonate, about 50% to about 99% by weight;
red iron oxide, about 0.5% to about 10% by weight;
herbal component, about 0.5% to about 20% by weight;
other ingredients, 0% to about 40% by weight.

Illustratively, the tooth powder comprises:

calcium carbonate, about 85% to about 95% by weight;
red iron oxide, about 1% to about 5% by weight;
herbal component, about 1% to about 10% by weight;
other ingredients, 0% to about 5% by weight.

Other ingredients can include, for example, one or more nonbotanical flavor enhancing agents such as a natural or artificial sweetener (for example, any sweetener mentioned hereinbelow) and/or salt. Optionally, the tooth powder can comprise any suitable further ingredient as more fully detailed below.

In some embodiments, the composition is in a dentifrice form other than a tooth powder, in which case additional ingredients as conventionally used in such dentifrice forms are generally required. Any dentifrice form can be used, but in general a form adapted for application to teeth with action that permits abrasion (e.g., brushing or chewing) is preferred. Such forms include, for example, gel and paste dentifrices and chewable preparations such as chewing gums.

A gel or paste dentifrice can comprise any oral care active(s) and/or carrier(s) known in the art, for example nonbotanical active(s) and/or carrier(s), in addition to the components mentioned above. Classification herein of an ingredient as an active or a carrier ingredient is made for clarity and convenience, and no inference should be drawn that a particular ingredient necessarily functions in the composition in accordance with its classification herein.

Among useful oral care actives are those addressing, without limitation, appearance and structural changes to teeth, treatment and prevention of plaque, calculus, dental caries, cavities, abscesses, inflamed and/or bleeding gums, gingivitis, oral infective and/or inflammatory conditions in general, tooth sensitivity, halitosis and the like. Thus, among useful actives for optional inclusion are fluoride ion sources, antibacterial agents, enhancing agents, whitening agents, anticalculus agents, stannous ion sources, zinc ion sources, antioxidants, sialagogues, breath freshening agents, antiplaque agents, anti-inflammatory agents, desensitizing agents, analgesics and nutrients. One active, or more than one active of the same or different classes, can optionally be present. Actives should be selected for compatibility with each other and with other ingredients of the composition.

In one embodiment the composition comprises at least one fluoride ion source useful, for example, as an anti-caries agent. Any orally acceptable fluoride ion source can be used, including without limitation potassium, sodium and ammonium fluorides and monofluorophosphates, calcium fluoride, barium fluoride, zinc fluoride, stannous fluoride, copper (II) fluoride, indium fluoride and the like. Water-soluble fluoride ion sources are typically used. One or more fluoride ion sources are optionally present in an amount providing a total of about 0.0025% to about 2%, for example about 0.005% to about 1% or about 0.01% to about 0.3%, of fluoride ions by weight of the composition.

In a further embodiment the composition comprises at least one antibacterial agent. Any orally acceptable antibacterial agent can be used, including without limitation halogenated diphenylethers such as triclosan or 2,2'-dihydroxy-5,5'-dibromodiphenylether, 8-hydroxyquinoline and salts thereof, copper (II) compounds such as copper (II) chloride, fluoride, sulfate and hydroxide, phthalic acid and salts thereof such as magnesium monopotassium phthalate, chlorhexidine, alexidine, hexetidine, sanguinarine, benzalkonium chloride, salicylanilide, domiphen bromide, alkylpyridinium salts such as cetylpyridinium salts (e.g., cetylpyridinium chloride (CPC) and combinations of CPC with zinc and/or enzymes), tetradecylpyridinium chloride and N-tetradecyl-4-ethylpyridinium chloride, parabens such as methylparaben and propylparaben, octenidine, iodine, sulfonamides, bisbiguanides, phenolics, piperidino derivatives such as delmopinol and octapinol, zinc ion sources, phenol, thymol, eugenol, menthol, geraniol, carvacrol, citral, eucalyptol, catechol, 4-allylcatechol, hexyl resorcinol, 2,2'-methylene bis(4-chloro-6-bromophenol), methyl salicylate, antibiotics such as augmentin, amoxicillin, tetracycline, doxycycline, minocycline, metronidazole, neomycin, kanamycin and clindamycin, and the like. In a particular embodiment, the composition comprises at least one antibacterial agent selected from the group consisting of triclosan, parabens, cetylpyridinium salts and combinations thereof.

In a still further embodiment the composition comprises at least one enhancing agent, for example to enhance retention of active agents by oral surfaces such as dental and gingival surfaces. Any orally acceptable antibacterial enhancing agent can be used, including without limitation polycarboxylate polymers, polyvinylmethylether/maleic anhydride (PVME/MA) copolymers, polyvinylphosphonic acid (PVPA), silicone polymers and copolymers, chitosan and combinations thereof.

In a still further embodiment the composition may contain at least one whitening agent. Any orally acceptable whitening agent can be used, including without limitation peroxy compounds, chlorine dioxide, chlorites and hypochlorites. For example, chlorites and hypochlorites of alkali and alkaline earth metals such as lithium, potassium, sodium, magnesium, calcium and barium can be used. Alternatively or in addition, one or more peroxy compounds can be used. Peroxy compounds include hydrogen peroxide, peroxides of alkali and alkaline earth metals, organic peroxy compounds and peroxy acids and salts thereof. Any orally acceptable compound that delivers a perhydroxy ($-OOH^-$) ion is useful. Peroxides of alkali and alkaline earth metals include lithium peroxide, potassium peroxide, sodium peroxide, magnesium peroxide, calcium peroxide and barium peroxide. Organic peroxy compounds include, for example, carbamide peroxide (also known as urea hydrogen peroxide), glyceryl hydrogen peroxide, alkyl hydrogen peroxides, dialkylperoxides, alkyl peroxy acids, peroxy esters, diacyl peroxides, benzoyl peroxide, monoperoxyphthalate and the like. Peroxy acids and their salts include organic peroxy acids such as alkyl peroxy acids and monoperoxyphthalate, as well as inorganic peroxy acid salts including persulfate, dipersulfate, percarbonate, perphosphate, perborate and persilicate salts of alkali and alkaline earth metals such as lithium, potassium, sodium, magnesium, calcium and barium. Peroxy compounds may be incompatible with the herbal component of the composition, thus if a peroxy compound is included as a whitening agent in the composition it should be segregated from the herbal component, for example by use of a dual-chamber dispensing container, by encapsulation or by some other means.

In a still further embodiment the composition comprises at least one anticalculus agent. Any orally acceptable anticalculus agent can be used, including without limitation phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and salts of any of these agents, for example their alkali metal and ammonium salts. Useful inorganic phosphate and polyphosphate salts illustratively include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and the like, wherein sodium can optionally be replaced by potassium or ammonium.

In a still further embodiment the composition comprises at least one stannous ion source useful, for example, in helping reduce gingivitis, plaque, caries or sensitivity. Any orally acceptable stannous ion source can be used, including without limitation stannous fluoride, other stannous halides such as stannous chloride dihydrate, organic stannous carboxylate salts such as stannous formate, acetate, gluconate, lactate, tartrate, oxalate, malonate and citrate, stannous ethylene glyoxide and the like. One or more stannous ion sources are optionally and illustratively present in a total amount of about 0.01% to about 10%, for example about 0.1% to about 7% or about 1% to about 5% by weight of the composition.

In a still further embodiment the composition comprises at least one zinc ion source useful, for example, as an antimicrobial, anticalculus or breath-freshening agent. Any orally acceptable zinc ion source can be used, including without limitation zinc citrate, zinc sulfate, zinc glycinate, sodium zinc citrate and the like. One or more zinc ion sources are optionally and illustratively present in a total amount of about 0.05% to about 3%, for example about 0.1% to about 1%, by weight of the composition.

In a still further embodiment the composition comprises at least one antioxidant. Any orally acceptable antioxidant can be used, including without limitation butylated hydroxyanisole (BHA), butylated hydroxytoluene (BHT), vitamin A, carotenoids, vitamin E, flavonoids, polyphenols, ascorbic acid, chlorophyll, melatonin and the like.

In a still further embodiment the composition comprises a sialagogue (saliva stimulating agent), useful for example in amelioration of dry mouth. Any orally acceptable sialagogue can be used, including without limitation food acids such as citric, lactic, malic, succinic, ascorbic, adipic, fumaric and tartaric acids.

In a still further embodiment the composition comprises a breath freshening agent. Any orally acceptable breath freshening agent can be used, including without limitation zinc salts such as zinc gluconate, zinc citrate and zinc chlorite, α-ionone and the like.

In a still further embodiment the composition comprises an antiplaque, including plaque disrupting, agent. Any orally acceptable antiplaque agent can be used, including without limitation stannous, copper, magnesium and strontium salts, dimethicone copolyols such as cetyl dimethicone copolyol, papain, glucoamylase and glucose oxidase.

In a still further embodiment the composition comprises at least one anti-inflammatory agent. Any orally acceptable anti-inflammatory agent can be used, including without limitation steroidal agents such as flucinolone and hydrocortisone, and nonsteroidal agents (NTHEs) such as ketorolac, flurbiprofen, ibuprofen, naproxen, indomethacin, diclofenac, etodolac, indomethacin, sulindac, tolmetin, ketoprofen, fenoprofen, piroxicam, nabumetone, aspirin, diflunisal, meclofenamate, mefenamic acid, oxyphenbutazone and phenylbutazone.

In a still further embodiment the composition comprises at least one desensitizing agent. Potassium salts such as potassium nitrate are illustratively useful in this regard, as is sodium nitrate. Alternatively or in addition a local or systemic analgesic such as aspirin, codeine, acetaminophen, sodium salicylate or triethanolamine salicylate can be used.

In a still further embodiment the composition comprises at least one nutrient. Suitable nutrients include vitamins, minerals and amino acids.

Among useful carriers for optional inclusion in a gel or paste dentifrice composition are diluents, abrasives other than calcium carbonate, bicarbonate salts, pH modifying agents, surfactants, foam modulators, thickening agents, viscosity modifiers, humectants, sweeteners, flavorants and colorants. One carrier material, or more than one carrier material of the same or different classes, can optionally be present. Carriers should be selected for compatibility with each other and with other ingredients of the composition.

In one embodiment the composition comprises at least one diluent, for example water.

In a further embodiment the composition comprises at least one abrasive in addition to the calcium carbonate. Any orally acceptable abrasive can be used, but type, fineness (particle size) and amount of abrasive should be selected so that tooth enamel is not excessively abraded in normal use of the composition. Suitable abrasives for use together with calcium carbonate in a composition of the invention include without limitation silica, for example in the form of silica gel, hydrated silica or precipitated silica, alumina, insoluble phosphates, resinous abrasives such as urea-formaldehyde condensation products and the like. Among insoluble phosphates useful as abrasives are orthophosphates, polymetaphosphates and pyrophosphates. Illustrative examples are dicalcium orthophosphate dihydrate, calcium pyrophosphate, β-calcium pyrophosphate, tricalcium phosphate, calcium polymetaphosphate and insoluble sodium polymetaphosphate. If an abrasive other than the calcium carbonate is present, the calcium carbonate preferably constitutes at least about 50%, for example at least about 75% or at least about 90%, by weight of all abrasives in the composition. Average particle size of any abrasive other than calcium carbonate that may be present is generally about 0.1 to about 30 µm, for example about 1 to about 20 µm or about 5 to about 15 µm. In one embodiment, the composition comprises substantially no abrasive other than calcium carbonate.

In a still further embodiment the composition comprises at least one bicarbonate salt, useful for example to impart a "clean feel" to teeth and gums due to effervescence and release of carbon dioxide. Any orally acceptable bicarbonate can be used, including without limitation alkali metal bicarbonates such as sodium and potassium bicarbonates, ammonium bicarbonate and the like.

In a still further embodiment the composition comprises at least one pH modifying agent. Such agents include acidifying agents to lower pH, basifying agents to raise pH and buffering agents to control pH within a desired range. For example, one or more compounds selected from acidifying, basifying and buffering agents can be included to provide a pH of about 2 to about 10, or in various illustrative embodiments about 2 to about 8, about 3 to about 9, about 4 to about 8, about 5 to about 7, about 6 to about 10, about 7 to about 9, etc. Any orally acceptable pH modifying agent can be used, including without limitation carboxylic, phosphoric and sulfonic acids, acid salts (e.g., monosodium citrate, disodium citrate, monosodium malate, etc.), alkali metal hydroxides such as sodium hydroxide, carbonates such as sodium carbonate, bicarbonates, sesquicarbonates, borates, silicates, phosphates (e.g., monosodium phosphate, trisodium phosphate, pyrophosphate salts, etc.), imidazole and the like.

In a still further embodiment the composition comprises at least one thickening agent, useful for example to impart a desired consistency and/or mouth feel to the composition. Any orally acceptable thickening agent can be used, including without limitation carbomers, also known as carboxyvinyl polymers, carrageenans, cellulosic polymers such as hydroxyethylcellulose, carboxymethylcellulose (CMC) and salts thereof, e.g., CMC sodium, natural gums such as karaya, xanthan, gum arabic and tragacanth, colloidal magnesium aluminum silicate, colloidal silica and the like.

In a still further embodiment the composition comprises at least one viscosity modifier, useful for example to inhibit settling or separation of ingredients or to promote redispersibility upon agitation of a liquid composition. Any orally acceptable viscosity modifier can be used, including without limitation mineral oil, petrolatum, clays and organomodified clays, silica and the like.

In a still further embodiment the composition comprises at least one sweetener, useful for example to enhance taste of the composition. Any orally acceptable natural or artificial sweetener can be used, including without limitation dextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof, dipeptide-based intense sweeteners, cyclamates and the like.

In a still further embodiment the composition comprises, in addition to any flavoring ingredient of the herbal component, at least one flavorant, useful for example to enhance taste of the composition. Any orally acceptable flavorant can be used, including without limitation vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants and the like. Also encompassed within flavorants herein are ingredients that provide fragrance and/or other sensory effect in the mouth, including cooling or warming effects. Such ingredients illustratively include menthol, menthyl acetate, menthyl lactate, camphor, eucalyptus oil, eucalyptol, anethole, eugenol, cassia, oxanone, α-irisone, propenyl guaiethol, thymol, linalool, benzaldehyde, cinnamaldehyde, N-ethyl-p-menthan-3-carboxamine, N,2,3-trimethyl-2-isopropylbutanamide, 3-(1-menthoxy)-propane-1,2-diol, cinnamaldehyde glycerol acetal (CGA), menthone glycerol acetal (MGA) and the like.

In a still further embodiment the composition comprises, in addition to the red iron oxide, at least one colorant. Colorants herein include pigments, dyes, lakes and agents imparting a particular luster or reflectivity such as pearling agents. Any orally acceptable colorant can be used, including without limitation talc, mica, magnesium carbonate, magnesium silicate, magnesium aluminum silicate, silica, titanium dioxide, zinc oxide, yellow, brown and black iron oxides, ferric ammonium ferrocyanide, manganese violet, ultramarine, titaniated mica, bismuth oxychloride and the like.

Compositions of the invention can be prepared by any conventional process for preparing dentifrices. Illustratively, a tooth powder of the invention can be prepared as follows.

Natural calcium carbonate from a suitable mineral source, e.g., chalk, is pulverized by any suitable mechanical method to a desired particle size range as indicated herein. If necessary, the pulverized calcium carbonate is screened to remove over- and/or undersized particles. (If precipitated calcium carbonate is used, the pulverizing and/or screening steps may not be necessary.) Red iron oxide of a purified grade is added and thoroughly mixed with the calcium carbonate. Addition of the red iron oxide can take place at any stage in the process, including before or after the calcium carbonate is pulverized. Other particulate components, for example comminuted crude botanicals, can likewise be added at any stage if required. Botanical extracts in liquid form such as oils are added as a coating to the calcium carbonate particles, for example in a ribbon blender. Typically, the liquid extracts (if more than one is required) are first combined into a single liquid premix and applied by spraying to the calcium carbonate. Addition of the liquid extracts should occur at a rate suitable to avoid particle agglomeration. A fine spray, for example having a droplet size of about 5 to about 20 μm, will generally be found suitable. It is generally desirable to maintain a calcium carbonate bed during the coating process at a temperature of about 20° C. to about 60° C.

A dentifrice composition of the invention can be applied to teeth and/or gums by any conventional method, preferably one that involves agitation to permit abrasive action. In one embodiment the composition is applied by brushing.

EXAMPLE

A tooth powder is prepared, for example in a ribbon blender by a process substantially as described above, having the following composition (all percentages are by weight):
 natural calcium carbonate 89-93%
 red iron oxide 2-8%
 camphor 0.5-1.5%
 *Terminalia chebula* 0.5-2.5%
 clove oil 0.5-1.5%
 basil oil 0.002-0.01%
 neem oil 0.005-0.02%
 oleoresin piperine 0.2-0.6%
 oleoresin ginger 0.05-0.2%
 salt 0.2-0.7%
 saccharin 0-0.6%
 flavor 0.2-1%

The composition exhibits good flavor delivery and has an abrasivity as determined by REA value of less than 4×. The red iron oxide is found not to stain teeth.

The blend of botanicals and extracts thereof in the composition is believed to impart pain relieving, astringency, antibacterial and anti-inflammatory properties. Camphor is believed to be a pain relieving agent in the composition and also imparts an attractive aroma to the composition. Astringency of the composition arises at least from the *T. chebula* component. Salt reduces bitterness attributable to some of the other ingredients. Oleoresin piperine is a known remedy for sore throat and oleoresin ginger is believed to have anti-inflammatory activity.

We claim:

1. A tooth powder composition comprising:
   (a) calcium carbonate having properties of particle size and angularity effective to provide mild abrasivity to dental enamel, wherein the particle size is selected from the group consisting of about 0.5 to about 30 μm and about 1 to about 15 μm;
   (b) an effective amount of a red iron oxide of low abrasivity which imparts a red color to the composition; and
   (c) a herbal component comprising at least one botanical agent or extract thereof,
   wherein the calcium carbonate and red iron oxide are present in a weight ratio selected from the group consisting of about 5:1 to about 100:1 and about 10:1 to about 50:1.

2. The composition of claim 1, wherein the calcium carbonate is finely ground natural calcium carbonate.

3. The composition of claim 1, wherein the red iron oxide is natural red iron oxide of a purified grade.

4. The composition of claim 1, wherein the herbal component is present in an amount, by weight, of about 0.5 to about 10 parts per 100 parts of calcium carbonate and red iron oxide.

5. The composition of claim 1, wherein the at least one botanical or extract thereof is selected from the group consisting of achyranthes, aloe, anise, aristolochia, arnica, bakula, banyan, basil, betel, black pepper, camphor, catechu, celandine, chamomile, chebula, Chinese skullcap, cinnamon, citrus, clove, dill, echinacea, eucalyptus, fennel, gardenia, ginger, grape, green tea, hop, houttuynia, Indian mulberry, juniper, lemongrass, licorice, long pepper, madhuca, magnolia, marigold, mastic, melilot, milfoil, myrrh, neem, neroli, nutmeg, oak gall, oolong tea, parsley, peelu, peppermint, pine, pomegranate, prickly acacia, rhatany, rosemary, saffron, sage, sandalwood, spearmint, spilanthes, star anise, thyme, tomar, tulsi, turmeric, usnea, vajradanti, walnut, wintergreen, extracts thereof and combinations thereof.

6. The composition of claim 1, wherein the herbal component further comprises at least one flavorant botanical or extract thereof.

7. The composition of claim 1, wherein the herbal component comprises a complex of botanicals and/or extracts thereof cooperating to promote oral health.

8. The composition of claim 1, further comprising at least one nonbotanical flavor enhancing agent.

9. The composition of claim 8, wherein the at least one nonbotanical flavor enhancing agent comprises one or more of salt and a natural or artificial sweetener.

10. The composition of claim 1, comprising about 85% to about 95% by weight natural calcium carbonate, about 1% to about 5% by weight natural red iron oxide, and about 1% to about 10% by weight of a herbal component that comprises basil oil, black pepper oleoresin, camphor, chebula, clove oil, ginger oleoresin and neem oil.

11. The composition of claim 1, further comprising one or more nonbotanical ingredients independently selected from fluoride ion sources, stannous ion sources, zinc ion sources, antibacterial agents, anti bacterial enhancing agents, antioxidants, sialagogues, breath freshening agents, antiplaque agents, anticalculus agents, anti-inflammatory agents, desensitizing agents, whitening agents, analgesics and nutrients.

12. The composition of claim 11, comprising a fluoride ion source selected from the group consisting of potassium, sodium and ammonium fluorides and monofluorophosphates, calcium fluoride, barium fluoride, zinc fluoride, stannous fluoride, cuprous fluoride, indium fluoride and combinations thereof.

13. The composition of claim 11, comprising an antibacterial agent selected from the group consisting of triclosan, parabens, cetylpyridinium salts and combinations thereof.

14. The composition of claim 11, comprising an antibacterial enhancing agent selected from the group consisting of polycarboxylate polymers, PVME/MA copolymers, PVPA, silicone polymers and copolymers, chitosan and combinations thereof.

* * * * *